(12) United States Patent
Gunatillake et al.

(10) Patent No.: US 6,420,452 B1
(45) Date of Patent: Jul. 16, 2002

(54) SILICON-CONTAINING CHAIN EXTENDERS

(75) Inventors: Pathiraja A. Gunatillake, Mulgrave; Gordon Francis Meijs, Murrumbeena; Raju Adhikari, Clayton, all of (AU)

(73) Assignee: Aortech Biomaterials PTY LTD (AU)

( * ) Notice: Subject to any disclaimer, the term of this patent is extended or adjusted under 35 U.S.C. 154(b) by 0 days.

(21) Appl. No.: 09/483,165

(22) Filed: Jan. 14, 2000

Related U.S. Application Data

(63) Continuation-in-part of application No. PCT/AU98/00546, filed on Jul. 14, 1998.

(30) Foreign Application Priority Data

Jul. 14, 1997 (AU) .............................................. PO7878

(51) Int. Cl.$^7$ .............................................. C08G 18/06
(52) U.S. Cl. .......................... 523/105; 528/44; 528/75; 528/83; 528/85; 525/464; 525/410; 525/474
(58) Field of Search ............................. 528/44, 75, 83, 528/85; 525/464, 410, 474; 523/105

(56) References Cited

U.S. PATENT DOCUMENTS

| | | | |
|---|---|---|---|
| 4,647,643 A | 3/1987 | Zdrahala et al. ............... 528/28 |
| 5,130,461 A | * 7/1992 | Shinohara et al. | |
| 5,239,037 A | * 8/1993 | Krishnan | |
| 5,330,840 A | * 7/1994 | Chen et al. | |

FOREIGN PATENT DOCUMENTS

| | | | | |
|---|---|---|---|---|
| EP | 0385732 A1 | 9/1990 | ............. C07F/7/08 |
| EP | 0464844 A1 | 1/1992 | ............. C07F/7/08 |
| GB | 2092607 A | 8/1982 | ............. C07F/7/08 |
| JP | 61129187 | 6/1986 | ............. C07F/7/08 |
| JP | 02296832 A | 7/1990 | ............. C09G/77/45 |
| JP | 4025580 A | 1/1992 | ........ C09D/175/04 |
| JP | 04041493 A | 12/1992 | ............. C07F/7/08 |
| WO | WO 98/13405 | 4/1998 | ............. C08G/18/44 |

OTHER PUBLICATIONS

Omel'chenko, S. I., Sint. Fiz.–Khim. Polim. (1977), 21, 35–44.*

* cited by examiner

*Primary Examiner*—Robert Dawson
*Assistant Examiner*—Kuo-Liang Peng
(74) *Attorney, Agent, or Firm*—Schwegman, Lundberg, Woessner & Kluth, P.A.

(57) ABSTRACT

A polyurethane composition comprising a chain extender including a silicon-containing diol of the formula (I):

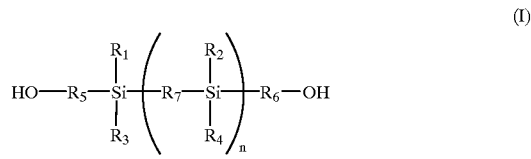

(I)

Figure 1A:
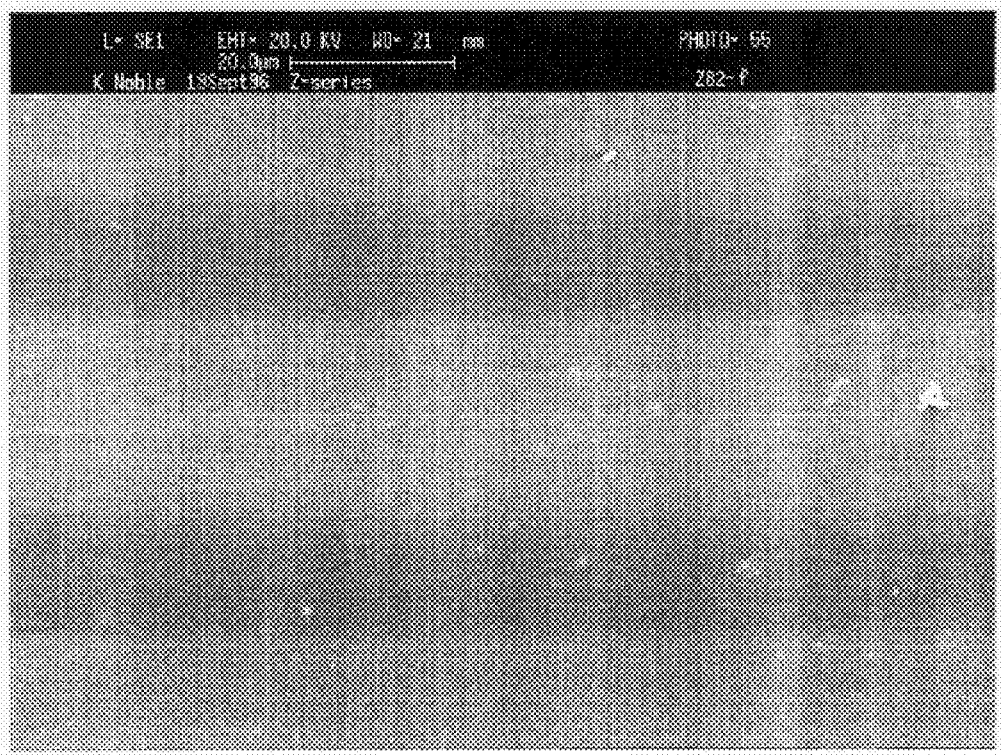

wherein
$R_1$, $R_2$, $R_3$, $R_4$, $R_5$, and $R_6$ are the same or different and selected from an optionally substituted straight chain, branched or cyclic, saturated or unsaturated hydrocarbon radical;

$R_7$ is a divalent linking group or an optionally substituted straight chain, branched or cyclic, saturated or unsaturated hydrocarbon radical; and n is 0 or greater, preferably 2 or less.

48 Claims, 4 Drawing Sheets

SILICON-CONTAINING CHAIN EXTENDERS

CROSS-REFERENCE TO RELATED APPLICATIONS

This application is a continuation-in-part of International Patent Application No. PCT/AU98/00546, filed on Jul. 14, 1998, which in turn is an international filing of Australian Patent Application No. PO7878, filed on Jul. 14, 1997, both of which are incorporated herein by reference.

The present invention generally relates to silicon-containing chain extenders and their use in the preparation of polyurethane elastomeric compositions having improved properties. These polyurethane compositions are useful for a variety of applications, in particular the manufacture of medical devices, articles or implants which contact living tissues or bodily fluids.

Polyurethane elastomers are amongst the best performing synthetic polymers in medical implant applications. Their excellent mechanical properties coupled with relatively good biostability make them the choice materials for a number of medical implants including cardiac pacemakers, catheters, implantable prostheses, cardiac assist devices, heart valves and vascular grafts. The excellent mechanical properties of polyurethane elastomers are attributed to their two phase morphology resulting from microphase separation of soft and hard segments. In polyurethanes used for medical implants, the soft segment is typically formed from a polyether macrodiol such as poly(tetramethylene oxide) (PTMO) while the hard segment is derived from a diisocyanate such as 4,4'-methylenediphenyl diisocyanate (MDI) and a diol chain extender such as 1,4-butanediol (BDO).

The diol chain extender which is used to link up diisocyanates is a relatively small difunctional molecule of molecular weight between about 60 and 350. The structure of the chain extender makes a significant contribution to the physical properties of the polyurethane elastomers. The most commonly used diol chain extender is 1,4-butanediol.

Despite the long term use of polyurethane elastomers for applications such as cardiac pacemakers, in some cases the polyurethanes biodegrade causing surface or deep cracking, stiffening, erosion or the deterioration of mechanical properties such as flexural strength[1]. Elastomers with high flexibility and low Shore A Durometer hardness in particular degrade faster than the harder and more rigid grades. It is generally hypothesized that the degradation is primarily an in vivo oxidation process involving the polyether soft segment. The currently used medical polyurethanes are polyether-based and the most vulnerable site for degradation is the methylene group alpha to the ether oxygen[2] of the soft segment. Polyurethanes prepared with a lower amount of polyether component generally exhibit improved degradation resistance. However, such materials typically have high elastic modulus and are difficult to process making them less desirable for many implant applications. Pinchuk has recently reviewed the biostability of polyurethanes[3].

Non-PTMO based polyurethane formulations which show significantly improved in vivo degradation resistance as demonstrated by animal implant experiments have also recently been disclosed in the patent literature. These include polyurethane formulations based on polycarbonate macrodiols disclosed in U.S. Pat. No. 5,133,742 (Pinchuk) and U.S. Pat. No. 5,254,662 (Szycher) and polyether macrodiols with fewer ether linkages in U.S. Pat. No. 4,875,308 (Meijs et al). The aforementioned patents do not disclose polyurethane formulations which provide materials having flexural modulus, hardness and biostability comparable to those of silicon rubber while retaining high tensile strength, abrasion resistance and tear strength of typical polyurethane elastomers. Although the compositions disclosed in U.S. Pat. No. 5,254,662 provide materials with low elastic modulus and high tensile strength, since those compositions are based on polycarbonate macrodiols and aliphatic diisocyanates, their degradation resistance under in vivo conditions is questionable. Hergenrother et al[4] have demonstrated by animal implant experiments that aliphatic diisocyanate based polyurethanes degrade more than the aromatic diisocyanate based polyurethanes. There are also no examples provided in U.S. Pat. No. 5,254,662 to demonstrate the biostability of the disclosed low modulus elastomer compositions.

The conventional method of preparing polyurethane elastomers with low hardness and modulus is by formulation changes so as to have a relatively higher percentage of the soft segment component. However, the materials made this way generally have very poor mechanical properties and biostability. For example, it is reported[2,1] that Pellethane 2363-80A (Registered Trade Mark) which has a higher percentage of soft segment than that in the harder grade Pellethane 2363-55D (Registered Trade Mark), is significantly more prone to stress cracking in the biological environment. However, these reports do not disclose methods for formulating polyurethanes with hardness lower than 80 A while retaining good biostability and mechanical properties. Despite the good stability of silicone rubber in biological environments, its use in the medical implant area is limited by poor properties such as low abrasion resistance and low tensile and tear strengths.

Although the aforementioned non-PTMO based polyurethane elastomers address the issue of biostability, they do not provide methods of formulating polyurethanes having properties such as flexibility and biostability comparable to those of silicone rubber. The formulations disclosed in the above patents (except U.S. Pat. No. 5,254,662) typically have hardness in excess of Shore 80 A.

A requirement accordingly exists to develop polyurethanes having properties such as low durometer hardness, low flexural modulus, good processability and high resistance to degradation, without the disadvantages of silicone rubber such as poor tensile strength, abrasion resistance and tear strength. Such polyurethanes should also preferably have a good biostability for applications such as pacemaker leads, vascular grafts, heart valves and the like.

According to one aspect of the present invention there is provided a chain extender including a silicon-containing diol of the formula (I):

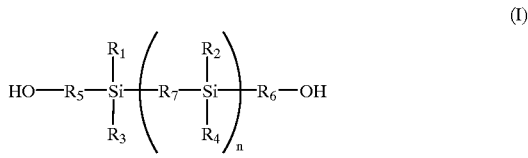

(I)

wherein
R$_1$, R$_2$, R$_3$, R$_4$, R$_5$, and R$_6$ are the same or different and selected from an optionally substituted straight chain, branched or cyclic, saturated or unsaturated hydrocarbon radical;

R$_7$ is a divalent linking group or an optionally substituted straight chain, branched or cyclic, saturated or unsaturated hydrocarbon radical; and n is 0 or greater, preferably 2 or less.

The present invention also provides use of the diol of the formula (I) defined above as a chain extender.

The present invention further provides the diol of the formula (I) as defined above when used as a chain extender.

The hydrocarbon radical for substituents $R_1$, $R_2$, $R_3$ and $R_4$ may include alkyl, alkenyl, alkynyl, aryl or heterocyclyl radicals. It will be appreciated that the equivalent radicals may be used for substituents $R_5$, $R_6$ and $R_7$ except that the reference to alkyl, alkenyl and alkynyl should be to alkylene, alkenylene and alkynylene, respectively. In order to avoid repetition, only detailed definitions of alkyl, alkenyl and alkynyl are provided hereinafter.

The term "alkyl" denotes straight chain, branched or mono- or poly-cyclic alkyl, preferably $C_{1-12}$ alkyl or cycloalkyl. Examples of straight chain and branched alkyl include methyl, ethyl, propyl, isopropyl, butyl, isobutyl, sec-butyl, amyl, isoamyl, sec-amyl, 1,2-dimethylpropyl, 1,1-dimethylpropyl, pentyl, hexyl, 4-methylpentyl, 1-methylpentyl, 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, heptyl, 5-methylhexyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethylpentyl, 1,2,3-trimethylbutyl, 1,1,2-trimethylbutyl, 1,1,3-trimethylbutyl, octyl, 6-methylheptyl, 1-methylheptyl, 1,1,3,3-tetramethylbutyl, nonyl, 1-, 2-, 3-, 4-, 5-, 6- or 7-methyloctyl, 1-, 2-, 3-, 4- or 5-ethylheptyl 1-, 2- or 3-propylhexyl, decyl, 1-, 2-, 3-, 4-, 5-, 6-, 7- and 8-methylnonyl, 1-, 2-, 3-, 4-, 5- or 6-ethyloctyl, 1-, 2-, 3- or 4-propylheptyl, undecyl 1-, 2-, 3-, 4-, 5-, 6-, 7-, 8- or 9-methyldecyl, 1-, 2-, 3-, 4-, 5-, 6- or 7-ethylnonyl, 1-, 2-, 3-, 4- or 5-propyloctyl, 1-, 2- or 3-butylheptyl, 1-pentylhexyl, dodecyl, 1-, 2-, 3-, 4-, 5-, 6-, 7-, 8-, 9- or 10-methylundecyl, 1-, 2-, 3-, 4-, 5-, 6-, 7- or 8-ethyldecyl, 1-, 2-, 3-, 4-, 5- or 6-propylnonyl, 1-, 2-, 3- or 4-butyloctyl, 1,2-pentylheptyl and the like. Examples of cyclic alkyl include cyclopropyl, cyclobutyl, cyclopentyl, cyclohexyl, cycloheptyl, cyclooctyl, cyclononyl, cyclodecyl and the like.

The term "alkenyl" denotes groups formed from straight chain, branched or mono- or poly-cyclic alkenes including ethylenically mono- or poly-unsaturated alkyl or cycloalkyl groups as defined above, preferably $C_{2-12}$ alkenyl. Examples of alkenyl include vinyl, allyl, 1-methylvinyl, butenyl, isobutenyl, 3-methyl-2-butenyl, 1-pentenyl, cyclopentenyl, 1-methylcyclopentenyl, 1-hexenyl, 3-hexenyl, cyclohexenyl, 1-heptenyl, 3 heptenyl, 1-octenyl, cyclooctenyl, 1-nonenyl, 2-nonenyl, 3-nonenyl, 1-decenyl, 3-decenyl, 1,3-butadienyl, 1,4-pentadienyl, 1,3-cyclopentadienyl, 1,3-hexadienyl, 1,4-hexadienyl, 1,3-cyclohexadienyl, 1,4-cyclohexadienyl, 1,3-cycloheptadienyl, 1,3,5-cycloheptatrienyl, 1,3,5,7-cycloocta-tetraenyl and the like.

The term "alkynyl" denotes groups formed from straight chain, branched, or mona or poly-cyclic alkynes. Examples of alkynyl include ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl, 5-hexynyl, 10-undecynyl, 4-ethyl-1-octyn-3-yl, 7-dodecynyl, 9-dodecynyl, 10-dodecynyl, 3-methyl-1-dodecyn-3-yl, 2-tridecynyl, 11-tridecynyl, 3-tetradecynyl, 7-hexadecynyl, 3-octadecynyl and the like.

The term "aryl" denotes single, polynuclear, conjugated and fused residues of aromatic hydrocarbons. Examples of aryl include phenyl, biphenyl, terphenyl, quatemphenyl, phenoxyphenyl, naphthyl, tetahydronaphthyl, anthracenyl, dihydroanthracenyl, benzanthracenyl, dibenzanthracenyl, phenantrenyl and the like.

The term "heterocyclyl" denotes mono- or poly-cyclic heterocyclyl groups containing at least one heteroatom selected from nitrogen, sulphur and oxygen. Suitable heterocyclyl groups include N-containing heterocyclic groups, such as, unsaturated 3 to 6 membered heteromonocyclic groups containing 1 to 4 nitrogen atoms, for example, pyrrolyl, pyrrolinyl, imidazolyl, pyrazolyl, pyridyl, pyrimidinyl, pyrazinyl, pyridazinyl, triazolyl or tetrazolyl; saturated 3 to 6-membered heteromonocyclic groups containing 1 to 4 nitrogen atoms, such as pyrrolidinyl, imidazolidinyl, piperdino or piperazinyl; unsaturated condensed heterocyclic groups containing 1 to 5 nitrogen atoms, such as, indolyl, isoindolyl, indolizinyl, benzimidazolyl, quinolyl, isoquinolyl, indazolyl, benzotriazolyl or tetrazolopyridazinyl; unsaturated 3 to 6-membered heteromonocyclic group containing an oxygen atom, such as, pyranyl or furyl unsaturated 3 to 6-membered hetermonocyclic group containing 1 to 2 sulphur atoms, such as, thienyl; unsaturated 3 to 6-membered heteromonocyclic group containing 1 to 2 oxygen atoms and 1 to 3 nitrogen atoms, such as, oxazolyl, isoazolyl or oxadiazolyl; saturated 3 to 6-membered heteromonocyclic group containing 1 to 2 oxygen atoms and 1 to 3 nitrogen atoms, such as, morpholinyl; unsaturated condensed heterocyclic group containing 1 to 2 oxygen atoms and 1 to 3 nitrogen atoms, such as, benzoxazolyl or benzoxadiazolyl; unsaturated 3 to 6-membered heteromonocyclic group containing 1 to 2 sulphur atoms and 1 to 3 nitrogen atoms, such as thiazolyl or thiadiazolyl; saturated 3 to 6-membered heteromonocyclic group containing 1 to 2 sulphur atoms and 1 to 3 nitrogen atoms, such as, thiadiazolyl; and unsaturated condensed heterocyclic group containing 1 to 2 sulphur atoms and 1 to 3 nitrogen atoms, such as benzothiazolyl or benzothiadiazolyl.

In this specification, "optionally substituted" means that a group may or may not be further substituted with one or more groups selected from oxygen, nitrogen, sulphur, alkyl, alkenyl, alkynyl, aryl, halo, haloalkyl, haloalkenyl, haloalkynyl, haloaryl, hydroxy, alkoxy, alkenyloxy, alkynyloxy, aryloxy, carboxy, benzyloxy, haloalkoxy, haloalkenyloxy, haloalkynyloxy, haloaryloxy, nitro, nitroalkyl, nitroalkenyl, nitroalkynyl, nitroaryl, nitroheterocyclyl, azido, amino, alkylamino, alkenylamino, alkynylamino, arylamino, benzylamino, acyl, alkenylacyl, alkynylacyl, arylacyl, acylamino, acyloxy, aldehydo, alkylsulphonyl, arylsulphonyl, alkylsulphonylamino, arylsulphonylamino, aIkylsulphonyloxy, arylsulphonyloxy, heterocyclyl, heterocycloxy, heterocyclylamino, haloheterocyclyl, alkylsulphenyl, arylsulphenyl, carboalkoxy, carboaryloxy, mercapto, alkylthio, arylthio, acylthio and the like.

Term "halo" denotes fluoro, chloro, bromo, or iodo, preferably fluoro. Examples of suitable fluoro radicals include trifluoropropyl, pentafluorobutyl, and heptafluoropropyl.

Suitable divalent linking groups for $R_7$ include 0, S and NR wherein R is hydrogen or an optionally substituted straight chain, branched or cyclic, saturated or unsaturated hydrocarbon radical.

Preferred silicon-containing diols are 1,3-bis (4hydroxybutyl)tetramethyl disiloxane (compound of formula (I) wherein $R_1$, $R_2$, $R_3$ and R4 are methyl, $R_5$ and $R_6$ are butyl and $R_7$ is O), 1,4-bis(3-hydroxypropyl)tetramethyl disilylethylene (compound of formula (I) wherein $R_1$, $R_2$, $R_3$ and $R_4$ are methyl, $R_5$ and $R_6$ are propyl and $R_7$ is ethylene) and 1-4-bis(3-hydroxypropyl)tetramethyl disiloxane.

The silicon-containing diol chain extenders can be conveniently prepared by methods reported in the literature[6].

Some of these compounds such as 1,3-bis(3-hydroxypropyl) tetramethyl disilylethylene (BPTD) and 1,3-bis(4-hydroxybutyl) tetramethyl disiloxane (BHTD) are available commercially. Others can be prepared by using hydrosilylation reaction of the appropriate hydroxy alkene and 1,1,3,3,-tetramethyldisiloxane using a catalyst such as Wilkinson's catalyst Some of the diols of formula (I) are novel per se. Thus, the present invention also provides a silicon-containing diol of the formula (I) defined above wherein $R_7$ is ethylene.

In a preferred embodiment, the diol of the formula (I) defined above is combined with a chain extender known in the art of polyurethane manufature.

According to another aspect of the present invention provides a chain extender composition including a silicone-containing diol of the formula (I) defined above and a chain extender known in the art of polyurethane manufacture.

The present invention also provides use of the composition defined above as a chain extender.

The present invention further provides the composition defined above when used as a chain extender.

The chain extender known in the art of polyurethane manufacture is preferably selected from 1,4-butanediol, 1,6-hexanediol, 1,8-octanediol, 1,9-nonanediol, 1,10-decanediol, 1,12-dodecanediol, 1,4-cyclohexanedimethanol, p-xylene glycol and 1,4-bis(2-hydroxyethoxy)benzene. 1,4 butanediol is particularly preferred.

The silicon chain extender and the known chain extender can be used in a range of molar proportions with decreasing tensile properties as the molar percentage of the silicon chain extender increases in the mixture. A preferred molar percentage of silicon chain extender is about 1 to about 50%, more preferably about 40%.

Although the preferred chain extender composition contains one known chain extender and one silicon-containing diol, it will be understood that mixtures containing more than one known chain extender and diol may be used in the chain extender composition.

The chain extender and chain extender composition of the present invention are particularly useful in preparing polyurethane elastomeric compositions.

According to a still further aspect of the present invention there is provided a polyurethane elastomeric composition which includes a segment derived from the chain extender or chain extender composition defined above.

The polyurethane elastomeric compositions of the present invention may be prepared by any suitable known technique. A preferred method involves mixing the chain extender or chain extender composition with a soft segment macrodiol and then reacting this mixture with a diisocyanate. The initial ingredients are preferably mixed at a temperature in the range of about 45 to about 100° C., more preferably about 60 to about 80° C. If desired, a catalyst such as dibutyl tin dilaurate at a level of about 0.001 to about 0.5 wt % based on the total ingredients may be added to the initial mixture. The mixing may occur in conventional apparatus or within the confines of a reactive extruder or continuous reactive injection molding machine.

Alternatively, the polyurethanes may be prepared by the prepolymer method which involves reacting a diisocyanate with the soft segment macrodiol to form a prepolymer having terminal reactive diisocyanate groups. The prepolymer is then reacted with the chain extender or chain extender composition.

Thus, the polyurethane elastomeric composition of the present invention may be further defined as comprising a reaction product of:

(i) a soft segment macrodiol;
(ii) a diisocyanate; and
(iii) the chain extender or chain extender composition defined above.

The soft segment macrodiol may be of any suitable type known in the art of polyurethane manufacture. Examples include polyethers, polyesters, polysiloxanes, polycarbonates or mixtures thereof Preferably, the soft segment is derived from a polysiloxane macrodiol and a polyether macrodiol.

A suitable polysiloxane is polydimethyl siloxane (PDMS). The polysiloxane macrodiols may be obtained as commercially available products such as X-22-160AS from Shin Etsu or prepared according to known procedures[7]. The preferred molecular weight range of the polysiloxane macrodiol is about 200 to about 5000, preferably about 300 to about 3000.

Suitable polyether macrodiols include those represented by the formula (II)

wherein
m is an integer of 4 or more, preferably 5 to 18; and
p is an integer of 2 to 50.

Although conventional polyether macrodiols such as PTMO can be used, the more preferred macrodiols and their preparation are described in Gunatillake et al[8] and U.S. Pat. No. 5,403,912. Polyethers such as PHMO described in these references are more hydrophobic than PTMO and are more compatible with polysiloxane macrodiols. The preferred molecular weight range of the polyether macrodiol is about 200 to about 5000, more preferably about 200 to about 1200.

Preferably, the diisocyanate is selected from one or more of 4,4'-methylenediphenyl diisocyanate MDI), methylene bis (cyclohexyl) diisocyanate (H12MDI), p-phenylene diisocyanate (p-PDI), trans-cyclohexane-1, 4diisocyanate (CHDI) or a mixture of the cis and trans isomers, 1,6-hexamethylene diisocyanate (DICH), 2,4-toluene diisocyanate (2,4-TDI) or its isomers or mixtures thereof p-tetramethylxylene diisocyanate (p-TMXDI) and m-tetramethylxylene diisocyanate (m-TMXDI). MDI is particularly preferred.

A particularly preferred polyurethane elatomeric composition of the present invention comprises a reaction product of:

(i) macrodiols including:
   (a) polysiloxane macrodiol; and
   (b) polyether macrodiol;
(ii) MDI; and
   (iii) chain extender composition including 1,4-butanediol and a silicon chain extender selected from 1,3-bis(4-hydroxybutyl)tetramethyl disiloxane and 1,4-bis(3-hydroxypropyl)tetramethyl disilylethylene and 1-4-bis(3-hydroxypropyl)tetramethyl disiloxane.

Preferably, the silicon chain extender is present in an amount of about 40 mol % of the chain extender composition.

The methods described above do not cause premature phase separation and yield polymers that are compositionally homogeneous and transparent having high molecular weights. These methods also have the advantage of not requiring the use of any solvent to ensure that the soft and hard segments are compatible during synthesis.

The polyurethane may be processed by conventional methods such as extrusion, injection and compression moulding without the need of added processing waxes. If desired, however, conventional polyurethane processing additives such as. catalysts, antioxidants, stablisers, lubricants, dyes, pigments, inorganic and/or organic fillers and reinforcing materials can be incorporated into the polyurethane during preparation. Such additives are preferably added to the soft segment macrodiol.

The soft segment macrodiol, diisocyanate and the chain extender or chain extender composition may be present in certain preferred proportions. The preferred level of hard segment (i.e. diisocyanate and chain extender) in the composition is about 40 to about 60 wt %. The weight ratio of polysiloxane to polyether in the preferred soft segment may be in the range of from 1:99 to 99:1. A particularly preferred ratio of polysiloxane to polyether which provides increased degradation resistance, stability and clarity is 80:20.

The polyurethane elastomeric composition of the present invention is particularly useful in preparing materials having good mechanical properties, in particular biomaterials.

According to another aspect of the present invention there is provided a material. having improved mechanical properties, clarity, processability and/or degradation resistance comprising a polyurethane elastomeric composition which includes a chain extender or chain extender composition defined above.

The present invention also provides use of the polyurethane elastomeric composition defined above as a material having improved mechanical properties, clarity, processability and/or degradation resistance.

The present invention fiber provides the polyurethane elastomeric composition defined above when used as a material having improved mechanical properties, clarity, processability and/or degradation resistance.

The mechanical properties which are improved include tensile strength, tear strength, abrasion resistance, Durometer hardness, flexural modulus and related measures of flexibility or elasticity.

The improved resistance to degradation includes resistance to free radical, oxidative, enzymatic and/or hydrolytic processes and to degradation when implanted as a biomaterial.

The improved processability includes ease of processing by casting such as solvent casting and by thermal means such as extrusion and injection molding, for example, low tackiness after extrusion and relative freedom from gels.

There is also provided a degradation resistant material which comprises the polyurethane elastomeric composition defined above.

The polyurethane elastomeric composition of the present invention shows good elastomeric properties. It should also have a good compatibility and stability in biological environments, particularly when implanted in vivo for extended periods of time.

According to another aspect of the present invention there is provided an in vivo degradation resistant material which comprises the polyurethane elastomeric composition defined above.

The polyurethane elastomeric composition may also be used as a biomaterial. The term "biomaterial" is used herein in its broadest sense and refers to a material which is used in situations where it comes into contact with the cells and/or bodily fluids of living animals or humans.

The polyurethane elastomeric composition is therefore useful in manufacturing medical devices, articles or implants.

Thus, the present invention still further provides medical devices, articles or implants which are composed wholly or partly of the polyurethane elastomeric composition defined above.

The medical devices, articles or implants may include cardiac pacemakers, defibrillators and other electromedical devices, catheters, cannulas, implantable prostheses, cardiac assist devices, heart valves, vascular grafts, extra-corporeal devices, artificial organs, pacemaker leads, defibrillator leads, blood pumps, balloon pumps, A-V shunts, biosensors, membranes for cell encapsulation, drug delivery devices, wound dressings, artificial joints, orthopaedic implants, soft tissue replacements, intraocular lenses, optical devices, tissue engineering products, and ENT implants.

It will be appreciated that polyurethane elastomeric compositions having properties optimised for use in the construction of various medical devices, articles or implants will also have other non-medical applications. Such applications may include their use in the manufacture of artificial leather, shoe soles; cable sheathing; varnishes and coatings; structural components for pumps, vehicles, etc; mining ore screens and conveyor belts; laminating compounds, for example in glazing; textiles; separation membranes; sealants or as components of adhesives.

Thus, the present invention extends to the use of the polyurethane elastomeric composition defined above in the manufacture of devices or articles.

The present invention also provides devices or articles which are composed wholly or partly of the polyurethane elastomeric composition defined above.

The invention will now be described with reference to the following examples. These examples are not to be construed as limiting the invention in any way.

Figure 1B:
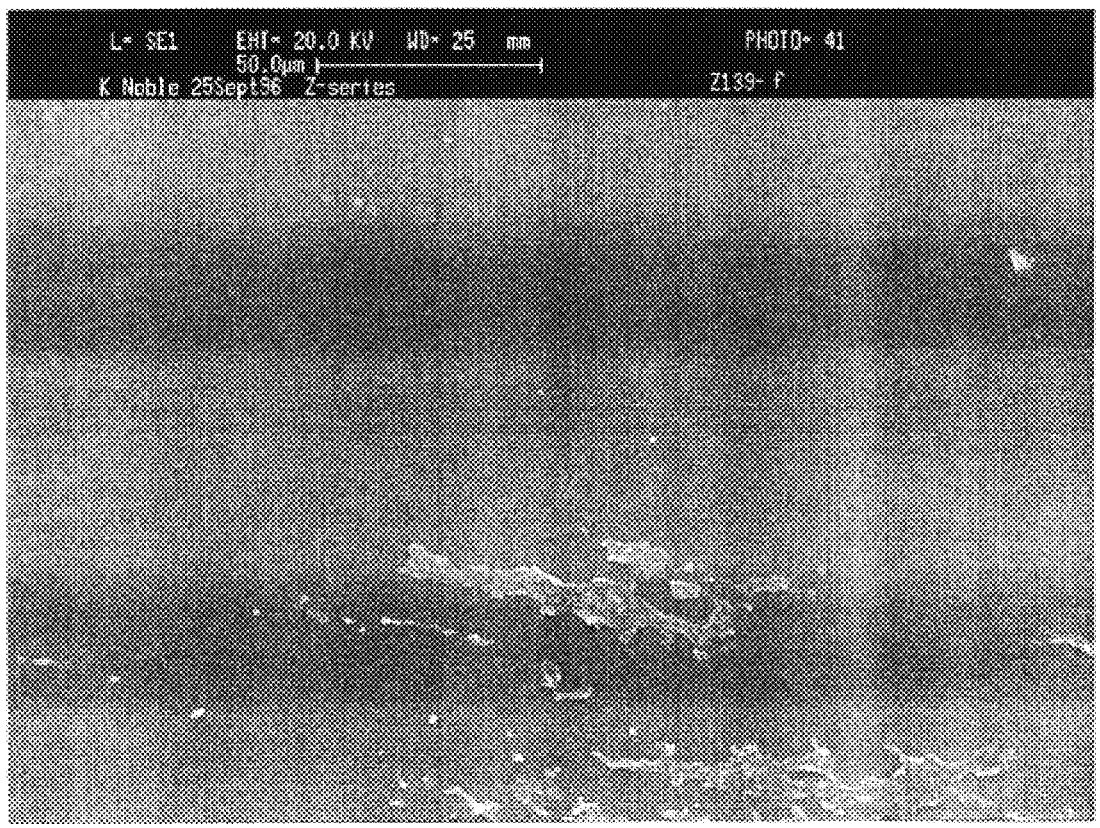
Figure 2A:
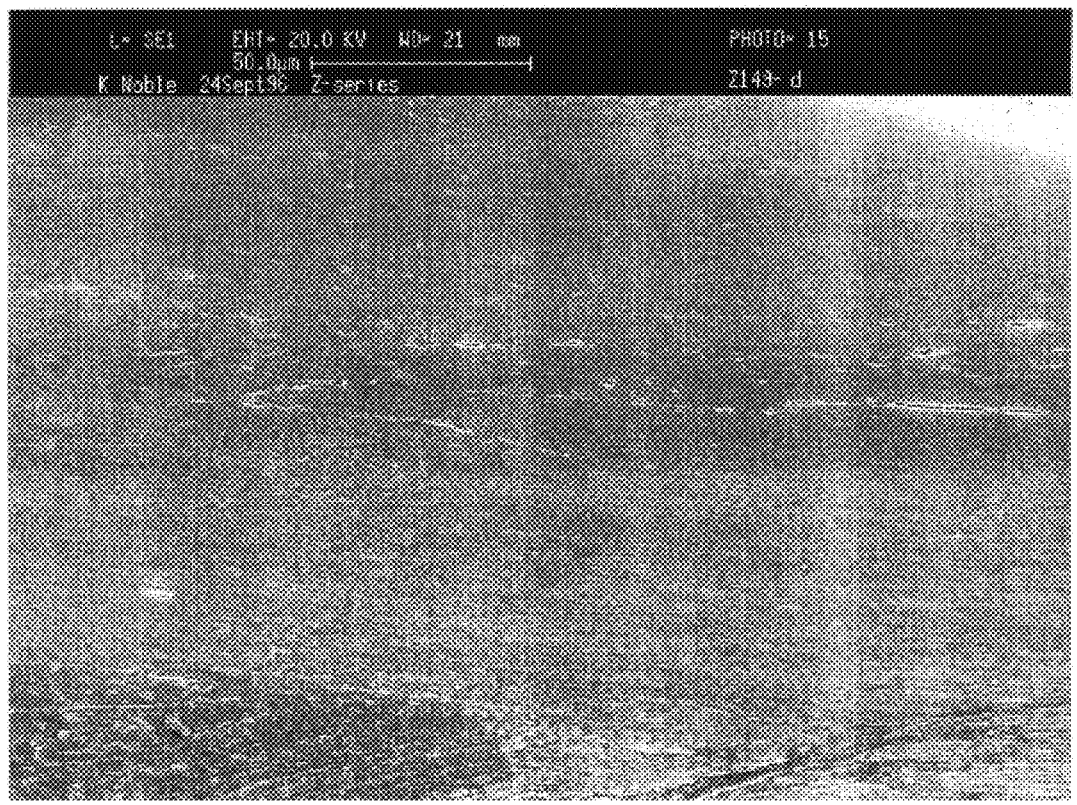
Figure 2B:
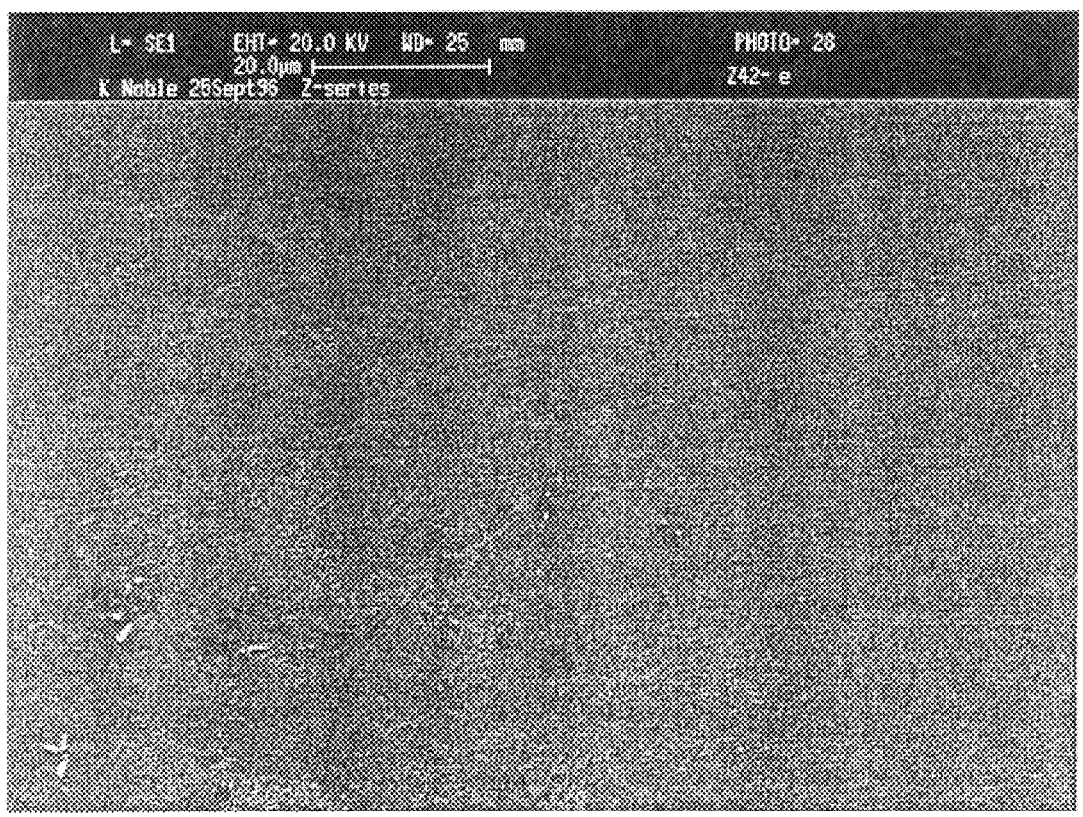

In the examples, reference will be made to the accompanying drawings in which:

FIGS. 1a and 1b are two photomicrographs of a polyurethane composition in Example 1 explanted after three months; and FIGS. 2a and 2b are two micrographs of a commercial Pellethane 2363-55D explanted after three months.

EXAMPLE 1

A polyurethane composition based on a mixture of PDMS/PHMO, a mixture of BDO and BHTD, and MDI was prepared by a one-step bulk polymerisation procedure.

α,ω-bis (6-hydroxyethoxypropyl)polydimethylsiloxane (Shin Etsu product x-22-160AS, MW 940.27) (PDMS) containing 0.1 wt % of tris(nonyltriphenyl)phosphine (TNPP) was dried at 105° C. for 15 h under vacuum (0.1 torr). Poly(hexamethylene oxide) (PHMO), prepared according to a method described by Gunafillake et al[8] and U.S. Pat. No. 5,403,912, was dried at 130° C. with 0.1 wt % TNPP (based on PHMO weight) under vacuum (0.1 torr) for 4 h. The molecular weight of the PHMO was 851.54. BHTD was degassed under vacuum (0.1 torr) at ambient temperature immediately before use to remove the cyclic impurities.

A mixture of dried PDMS (260.0 g), PHMO (65.00 g), 1,4-butanediol (16.14 g), dibutyl tin dilaurate catalyst (0.054 g), Irgawax (0.81 g) and Irganox 1010 (0.54 g) was placed into a 1L flask and degassed at 80° C. for 2 h under vacuum (0.2 torr). Separately degassed BHTD (33.256 g) was added to the flask containing the macrodiol mixture. This mixture (370.00 g) was weighed into a 1L polypropylene beaker and allowed to cool to 70° C. under nitrogen. Molten MDI (164.67 g) at 60° C. was weighed in a fume hood into 250 ml polypropylene beaker. The MDI was then quickly added with rapid stirring using a stainless steel spatula. The mixture, which was initially cloudy, tuned clear with mixing after about 10 sec. The viscous mixture was rapidly poured onto a teflon coated metal tray and cured in an oven under nitrogen at 100° C. Heating was discontinued after 4 h and the sheet of polyurethane was allowed to cool to ambient temperature over a period of about 15 h.

A sample of the polymer after drying for 15 h at 45° C. under vacuum (0.1 torr) was compression moulded at 180° C. to a 1 mm thick flat sheet for tensile testing. Dumbbells punched from the sheet were tensile tested using an Instron Model 4032 Universal Testing Machine.

The degradation resistance of the polyurethane composition described in example 1 was examined by a three month ovine implant experiment.

Polyurethane in example 1, Pellethane 2363-80A (Registered Trade Mark) and 2363-55D were compression moulded into sheets of 0.5 mm thickness. Specimens shaped as dumbbells were cut from the sheets and stretched over poly(methyl methacrylate) holders. This caused the central section to be strained to 250% of its original length. A polypropylene suture was firmly tied around the centre of each specimen. This caused a localised increase in stress in the specimen. The specimens attached to their holders were sterilised with ethylene oxide and implanted into the subcutaneous adipose tissue in the dorsal thoraco-lumbar region of adult crossbred wether sheep. This test method provides a means of assessing the resistance to biodegradation by environmental stress cracking.

After a period of three months the polyurethanes were retrieved. Attached tissue was carefully dissected away and the specimens were washed by soaking in 0.1M sodium hydroxide for 2 days at ambient temperature followed by rinsing in deionised water. The specimens were then dried in air and examined by scanning electron microscopy (SEM) for signs of pitting or cracking. The polyurethane sample showed no sign of stress cracking and while Pellethane 80A showed severe degradation. Since Pellethane 80A showed severe degradation visible to the naked eye, those samples were not examined by SEM. Representative scanning photomicrographs of the new polyurethane composition and Pellethane 55D are shown in FIGS. 1 and 2, respectively.

The mechanical properties of the material prepared in example 1 were examined and the results are shown in Table 1 with those of Pellethane 2363-80A (Registered Trade Mark) for comparison.

TABLE 1

| Property | Polyurethane - example 1 | Prior art soft Polyurethane (Pellethane - 2363A 80A)+ |
|---|---|---|
| Shore Hardness | 70A | 82A |
| Ultimate Tensile (MPa) | 28 | 33.7 |
| Elongation at break | 420 | 430 |
| Young's Modulus (MPa) | 9.6 | 13 |
| Tear Strength (N.mm$^{-1}$) | 51 | 72 |
| Flexural Modulus (MPa) | 14 | 26 |

+Results from testing of a commercial sample of Pellethane 2363-80A

The thermal processability of the polyurethane elastomer prepared according to the procedure in example 1 was evaluated by extrusion into a thin film (0.5 mm) using a single screw Brabeuder extruder. The polyurethane was dried at 45° C. under vacuum (0.1 torr) for 48 h prior to the extrusion. The material extruded easily into a clear and transparent film with no imperfections and the post extrusion tackiness was minimal with easy handling.

EXAMPLE 2

A polyurethane composition based on a mixture of PDMS/PHMO, a mixture of BDO and BHTD, and MDI was prepared by a two-step bulk polymerisation procedure without the use of the catalyst or other conventional additives used in example 1. The composition was based on an isocyanate index ([NCO/[OH]) of 1.03 and a hard segment weight percentage of 40.

PDMS (Shin Etsu product X-22-160AS, MW 937.83) was dried at 105° C. for 15 h under vacuum (0.1 torr). PHMO (MW 696.06) was dried at 130° C. under vacuum (0.1 torr) for 4 h prior to polymerisation.

Molten MDI (195.0 g) was weighed into a 2 L three necked round bottom flask fitted with an additional funnel, nitrogen inlet and a mechanical stirrer. The dried polyol mixture (240.0 g PDMS and 60.0 g PHMO) was weighed into the additional funnel and then added to MDI in the flask over a period of 30 min with stirring. During this time the reaction temperature was maintained at 70° C. The reaction was continued for further 2 h at 80° C. with stirring to form the prepolymer. The prepolymer (537.1 g) was then weighed into a 2 L polypropylene beaker and thoroughly mixed with the chain extenders BDO (16.82 g) for 2 min. The polymer was poured into a teflon coated pan and cured at 100° C. for 4 h in an oven under nitrogen.

The cured polyurethane after drying at 45° C. under vacuum (0.1 torr) was compression moulded at 180° C. into 2 mm thick flat sheets for testing tensile properties and flexural modulus, and 2 mm thick, 10.5 cm diameter discs for abrasion resistance. Tensile properties and flexural strength were tested on an Instron Model 4032 Universal Testing Machine while the abrasion resistance was tested on a Taber Model 503 Abraser using Calibrade H-22 abrading wheels and 1000 g wheel loading. The tensile test specimens were 10 cm long dumbbells with a 6 mm wide narrow section. The test results are summarised in Table 2 along with corresponding properties for a commercial sample of silicon rubber. Some properties of high tear strength silicon rubber as reported in the literature[5] are shown in Table 3 for comparison.

The clarity of the polyurethane composition in example 2 and commercial silicone rubber was measured on a Gardner Hazemeter Model UX10, using 2 mm thick films.

TABLE 2

| Property | Polyurethane of example 2 | Silicon Rubber† |
|---|---|---|
| Durometer Hardness (Shore A) | 70 | 65 |
| Tensile Strength (MPa) | 20 | 9.0 |
| Elongation at Break (%) | 890 | 410 |
| Young's Modulus (MPa) | 4.4 | 5.0 |
| Tear Strength (n/mm) | 57 | 45 |
| Flexural Modulus (MPa) | 14 | 17 |
| Abrasion (depth (mm)/3000 revolutions) | 0.06 | 0.09 |

†Results from testing of a commercial sample of Silicon Rubber

TABLE 3

| Property | Silicon Rubber | | |
| | 1 | 2 | 3 |
|---|---|---|---|
| Durometer Hardness (Shore A) | 50 | 50 | 50 |
| Tensile Strength (MPa) | 6.90 | 10.34 | 9.66 |
| Tear Strength (N/mm) (ASTM D624-54, Disc B) | 17.50 | 33.25 | 35.00 |

TABLE 3-continued

| | Silicon Rubber | | |
|---|---|---|---|
| Property | 1 | 2 | 3 |
| Abrasion (Rev/0.254 cm) (ASTM D1630 61) | 155 | 300 | 1600 |

TABLE 4

| Sample | Hazemeter Reading (% absorption) |
|---|---|
| Polyurethane of Example 2 | 7 |
| Commercial silicon rubber | 65 |
| Clear glass (microscope slide) | 1.5 |
| Parafilm | 50 |

The results in Tables 2, 3 and 4 clearly demonstrate that the composition of the present invention are superior to silicon rubber with respect to tensile strength, tear strength and abrasion resistance as well as film clarity.

EXAMPLE 3

1,4-bis(3-hydroxypropyl)-1,1,4,4-tetramethyl disilylethylene (HTDE) was prepared by a hydrosilylation procedure.

1,1,4,4,-Tetramethyldisilylethylene (50.0 g) and tris(triphenylphosphine) rhodium chloride (Wilkinson's catalyst, 0.005 g) were placed in a 500 ml round bottom flask fitted with a nitrogen inlet, addition funnel, a drying tube and a condenser. The flask was placed in an oil bath at 40° C. and allylalcohol (80.00 g) was added to the reaction mixture over a period of 30 min. After the addition was completed, the oil bath temperature was raised to 80° C. and continued reaction for 2 h. A sample of the reaction was analysed by IR spectroscopy. The absence of an Si—H band at 2160 cm$^{-1}$ was taken as the completion of the reaction. The product mixture was dissolved in $CH_2Cl_2$ and treated with charcoal to remove the catalyst. The product was purified by vacuum distillation and the fraction distilled at 135–137° C./0.1 torr was used for the preparation of polyurethane.

PDMS and PHMO were purified according to the procedures described in Example 1. PDMS (28.00 g), PHMO (7.00 g), BDO (2.433 g), HTDE (2.363 g) and dibutyl tin dilauarate (0.006 g) were weighed into a 100 ml poly (propylene) beaker and degassed at 80° C. for 2 h under vacuum (2 torr). Molten MDI (18.57 g) was quickly added to the contents in the beaker and stirred rapidly. The polymer was cured in the beaker at 100° C. for 4 h in an oven under nitrogen.

A sample of the polymer after drying for 15 h at 45° C. under vacuum (0.1 torr) was compression moulded at 180° C. to a 1 mm thick flat sheet for tensile testing. Dumbbells punched from the sheet were tensile tested on an Instron Model 4032 Universal Testing Machine: fail stress 17 MPa, fail strain 460%, Young's modulus 17.6 MPa, Shore hardness 79A and tear strength 51 N/mm.

EXAMPLE 4

1,3-bis(5-hydroxypentyl)-1,1,3,3-tetramethyldisiloxane (BHPD) and 1,3-bis(6-hydroxyhexyl)-1,1,3,3-tetramethyldisiloxane (BHHD) were prepared using procedures similar to that described in example 3.

Two polyurethanes were prepared using a one step procedure similar to that described in example 1. The polyurethane based on BHPD was prepared from PDMS (20.0 g), PHMO (5.0 g), MDI (12.72 g), BDO (1.209 g), BHPD (2.742 g) and catalyst dibutyl tin dilaurate (0.004 g). Likewise, a polyurethane based on BHHD was prepared from PDMS (20.0 g), PHMO (5.0 g), MDI (12.57 g), BDO (1.178 g), BHHD (2.914 g) and dibutyl tin dilaurate (0.004 g).

Samples of the two polymers after drying for 15 h at 45° C. under vacuum (0.1 torr) were compression moulded at 180° C. to a 1 mm thick flat sheet for testing tensile properties. Dumbbells punched from the sheets were tested on an Instron Model 4032 Universal Testing Machine. The polyurethane based on BHPD showed fail stress 19.5 MPa, fail strain 300%, stress at 100% elongation 7.2 MPa, Shore Hardness 67A and Young's modulus 11.2 MPa. Similarly, the polyurethane based on BHHD showed fail stress 22.2 MPa, fail strain 290%, Shore Hardness 60A and Young's modulus 12.7 MPa.

EXAMPLE 5

PDMS and PHMO were purified according to the procedures described in Example 1. PDMS (5.00 g), PHMO (20.0 g), BDO (2.04 g), BHTD (4.203 g) and dibutyl tin dilaurate (0.005 g) were weighed into a 100 ml poly(propylene) beaker and degassed at 80° C. for 2 h under vacuum (2 torr). Hydrogenated MDI (Aldrich, 18.76 g) was quickly added to the contents in the beaker and stirred rapidly. The polymer was cured in the beaker at 100° C. for 4 h in an oven under nitrogen.

The polymer after curing was colourless and transparent. A 1 mm thick sheet of the polymer was prepared by compression moulding at 180° C. Dumbbells punched from the sheet were tested for tensile properties on an Instron Model 4032 Universal Testing Machine: fail stress 18 MPa, fail strain 410%, stress at 100% elongation 2.3 MPa, Young's modulus 10 MPa and Shore hardness 60A.

EXAMPLE 6

This example illustrates the synthesis of a polyurethane composition using a PDMS macrodiol with a molecular weight of 1913.3 according to a two-step polymerisation procedure.

MDI (23.85 g) was weighed into a 250 mL three necked round bottom flask fitted with a dry nitrogen inlet, a mechanical stirrer and an addition funnel. The reaction flask was placed in an oil bath at 70° C. and the polyol mixture (40.00 g, PDMS molecular weight 1913.3 and 1000 g PHMO, molecular weight 700.16) was slowly added to MDI from the addition funnel over a period of 15 mil. After completion of the addition, the oil bath temperature was raised to 80° C. and reacted for 2 hours with stirring under a slow flow of nitrogen to complete the reaction. The prepolymer was then dissolved in anhydrous N,N-dimethyformamide (DMF) (440 mL) to make a 15% solution. The chain extender mixture, 1,4-butanediol (3.099 g) and 1,3bis(4-hydroxybutyl)tetramethyl disiloxane (6.387 g), was added to the prepolymer solution and reacted at 90° C. for 4h with stirring.

A 0.5 mm thick film was cast from the DMF solution of the polymer onto a Petrie dish and dried at 45° C. in an over for 48 h to remove the solvent. The cast film was clear and transparent. Test specimens were punched from the film for testing tensile properties and tear strength.

The polyurethane exhibited 22 MPa fail stress, 440% fail strain, 15 MPa Young's modulus, and 7 MPa stress at 100% elongation. The tear strength of the polyurethane was 60 N/mm.

EXAMPLE 7

This example illustrates that by varying the relative amounts of the silicon chain extender BHTD and the conventional chain extender BDO, polyurethanes with a range of mechanical properties could be synthesised. Eight polyurethanes were prepared by varying the chain extender composition (BHTD/BDO molar ratio) using a two-step polymerisation procedure similar to that described in Example 2.

Bishydroxyethoxypropylpolydimethylsiloxane (PDMS) (Shin-Etsu) and poly (hexamethylene oxide) (PHMO) were dried and degassed using a thin-film evaporator. 4,4'-methylenediphenyl diisocyanate (MDI, ICI Australia), 1,4-butanediol (BDO, GAF) and BHTD (Silar Laboratories) were used as received. The hard segment (MDI-based) was 40 wt-% while the soft segment was based on an 80/20 wt-% mixture of PDMS (MW 966) and PHMO (MW 715), respectively. Table 5 below lists the formulation details of each polyurethane prepared. Polyurethanes are designated as PU-XX where XX denotes the molar percentage of BHTD in the chain extender mixture.

TABLE 5

| Sample code | (PDMS/PHMO: 80/20) (g) | MDI (g) | BDO (g) | BHTD (g) |
|---|---|---|---|---|
| PU-0 | 300.0 | 170.4 | 29.61 | 0 |
| PU-10 | 300.0 | 166.0 | 25.28 | 8.68 |
| PU-20 | 300.0 | 162.1 | 21.37 | 16.51 |
| PU-30 | 300.0 | 158.55 | 17.83 | 23.62 |
| PU-40 | 300.0 | 155.3 | 14.60 | 30.09 |
| PU-60 | 300.0 | 149.7 | 8.94 | 41.44 |
| PU-80 | 300.0 | 144.79 | 4.13 | 51.08 |
| PU-100 | 300.0 | 140.64 | 0 | 59.36 |

Flat sheets of PU were prepared using compression moulding. Tensile test specimens punched from PU sheets were annealed at 100° C. for 10 h and allowed to condition to ambient temperature for one week before testing tensile properties. Tensile testing was conducted using an Instron Model 4032 Universal testing machine with a 1 kN load cell at a cross-head speed of 500 mm/min. The tensile properties of the polyurethanes are shown in Table 6 below.

TABLE 6

| Sample Code | Elong % | UTS MPa | YM MPa | Tear S. N/mm | FM MPa | SH (A) |
|---|---|---|---|---|---|---|
| PU-0 | 317 ± 4 | 23 ± 0.8 | 32 ± 3 | 61 ± 4 | 36 ± 2 | 85 |
| PU-10 | 356 ± 16 | 24 ± 1.5 | 22 ± 1 | 58 ± 2 | 27 ± 1.4 | 79 |
| PU-20 | 381 ± 6 | 24 ± 0.9 | 14 ± 0.5 | 52 ± 0.5 | 16 ± 3 | 75 |
| PU-30 | 378 ± 18 | 21 ± 1.6 | 9.3 ± 1.1 | 44 ± 3 | 12 ± 2 | 73 |
| PU-40 | 391 ± 5 | 20 ± 0.4 | 7.8 ± 0.4 | 43 ± 0.6 | 10 ± 0.5 | 70 |
| PU-60 | 420 ± 10 | 16 ± 1.3 | 7.4 ± 1.1 | 31 ± 0.9 | 7.9 ± 0.4 | 63 |
| PU-80 | 489 ± 15 | 13 ± 0.8 | 7.3 ± 1.2 | 23 ± 0.4 | 9 ± 0.1 | 64 |
| PU-100 | 547 ± 10 | 9.2 ± 0.4 | 13 ± 0.9 | 19 ± 0.3 | 17 ± 0.3 | 71 |

EXAMPLE 8

This example illustrates the synthesis of a polyurethane based on a new silicon chain extender bis(6-hydroxyethoxypropyl)tetramethyldisiloxane (BETD) [formula (I) wherein $R_5$ and $R_6$=—$CH_2CH_2OCH_2CH_2CH_2$; $R_7$=O; and $R_1$, $R_2$, $R_3$ and $R_4$=CH3].

BETD was synthesised by reacting 1,1,3,3=tetramethyldisiloxane and hydroxyethoxypropene in the presence of a hydrosilylation catalyst (Karstead's catalyst) using the procedure described in Example 3. A polyurethane based on a 60/40 molar composition of BDO and BETD was prepared using a two-step bulk polymerisation procedure.

Molten MDI (25.26 g) was weighed into a 250 mL three necked round bottom flask fitted with an addition funnel, nitrogen inlet and a mechanical stirrer. The dried polyol mixture (40.0 g PDMS and 10.0 g PHMO) was weighed into the addition funnel and then added to MDI in the flask over a period of 30 min with stirring. During this time the reaction temperature was maintained at 70° C. The reaction was continued for further 2 h at 80° C. with stirring to form the prepolymer. The prepolymer (70.00 g) was then weighed into a 250 mL polypropylene beaker and thoroughly mixed with chain extenders BDO (2.14 g) and BHTD (5.38 g) for 2 min. The polymer was poured into a teflon-coated pan and cured at 100° C. for 4 h in an oven under nitrogen.

A sample of the polyurethane after drying for 15 h at 45° C. under vacuum (0.1 torr) was compression moulded at 180° C. to a 1 mm thick flat sheet for tensile testing. Dumbbells punched from the sheet were tensile tested on an Instron Model 4032 Universal Testing Machine: fail stress 13 MPa, fail strain 415%, Young's modulus 7.5 MPa, Shore hardness 69, flexural modulus 9.5 MPa and tear strength 41 N/mm.

EXAMPLE 9

This example illustrates the synthesis of a polyurethane composition using a PDMS macrodiol with a molecular weight of 2955 according to a two-step procedure. MDI (23.10 g) was weighed into a 250 mL three necked round bottom flask fitted with a dry nitrogen inlet, a mechanical stirrer and an additional funnel. The reaction flask was placed in an oil bath at 70° C. and the polyol mixture (40.00 g PDMS molecular weight 2955.7 and 10.00 g PHMO, molecular weight 700.2) was slowly added to MDI from the addition funnel over a period of 15 min. After completion of the addition, the oil bath temperature was raised to 80° C. and reacted for 2 hours with stirring under a slow flow of nitrogen to complete the reaction. The prepolymer was dissolved in anhydrous N,N'-dimethylacetamide (DMAc) (330 mL) to make a 20 wt-% solution. The chain extender mixture, 1,4-butanediol (3.34 g) and 1,3-bis(4-hydroxybutyl)tetramethyldisiloxane (6.887 g) was added to the prepolymer solution and reacted at 90° C. for 4 h with stirring. A 0.5 mm thick film was cast from the DMF solution of the prepolymer onto a Petrie dish and dried at 45° C. in an oven for 48 h to remove the solvent. The cast film was clear and transparent. Test specimens were punched from the film for testing tensile properties and tear strength.

The polyurethane exhibited 21 MPa fail stress, 168% elongation at break, 62.64 Young's modulus and 55 N/mm tear strength.

REFERENCES

1. M. Szycher, *J. Biomat. Appl.*, Vol 3, pp 297–402, (1988).
2. M. Szycher and W. A. McArthur, Surface Fissuring of Polyurethanes Following In Vivo Exposure, In A. C. Fraker and C. D. Griffin, Eds. *Corrosion and Degradation of Implant Materials*, Philadelphia, Pa., ASTM STP 859, pp 308–321, (1985).
3. L. Pinchuk, *J. Biomater. Sci. Edn*, Vol 3 (3), pp 225–267, (1994).
4. R. W. Hergenrother and S. L. Cooper, *Mat. Res. Soc. Symp. Proc.*, Vol 252, pp 257–263, (1992).
5. K. E. Polmanteer, Advances in Silicon Rubber Technology in *Handbook of Elastomers*, A. K. Bhowmick and H. L. Stephens, Eds Marcel Dekker, Inc., pp 551–615, (1988).

6. F. Braun, L. Willner, M. Hess and R. Kosfeld, *J.Organomet. Chem.*, Vol 332, pp 63–68, (1987).
7. I. Yilgor, J. S. Riffle, W. P. Steckle, Jr., A. K. Banthia and J. E. McGrath, *Polym. Mater. Sci & Eng.*, Vol 50, pp 518–522, (1984).
8. P. A. Gunatillake, G. F. Meijs, R. C. Chatelier, D. M. McIntosh and E. Rizzardo, *Polym. Int.*, Vol 27, pp 275–283, (1992).

It will be appreciated that further modifications and alterations may be made to the embodiment described above without departing from the scope or spirit of the present invention.

What is claimed is:

1. A polyurethane composition comprising a reaction product of:
   (i) a soft segment macrodiol;
   (ii) a diisocyanate; and
   (iii) a chain extender including a silicon-containing diol of the formula (I):

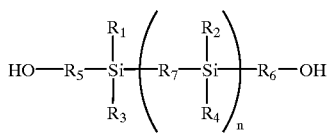

(I)

wherein $R_1$, $R_2$, $R_3$ and $R_4$ are independently an optionally substituted straight chain, branched or cyclic, saturated or unsaturated hydrocarbon radical;
   $R_5$ and $R_6$ are independently an optionally substituted straight chain, branched or cyclic alkylene, alkenylene, alkynylene or heterocyclic radical;
   $R_7$ is a divalent linking group of an optionally substituted straight chain, branched or cyclic, saturated or unsaturated hydrocarbon radical; and,
   n is 0 or greater.

2. A polyurethane composition as claimed in claim 1 wherein said soft segment macrodiol is polyether, polyester, polysiloxane, polycarbonate or mixtures thereof.

3. A polyurethane composition as claimed in claim 2 wherein the soft segment macrodiol is derived from a polysiloxane macrodiol and a polyether macrodiol.

4. A polyurethane composition as claimed in claim 2 wherein the soft segment macrodiol comprises a polysiloxane macrodiol having a molecular weight in the range of 200 to 5000.

5. A polyurethane composition as claimed in claim 3 wherein the molecular weight of the macrodiol is in the range of 300 to 3000.

6. A polyurethane composition as claimed in claim 2 wherein the soft segment macrodiol is derived from polydimethyl siloxane.

7. A polyurethane composition as claimed in claim 2 wherein the soft segment macrodiol includes a polyether macrodiol of formula (II):

(II)

wherein,
   m is an integer of 4 or more; and
   p is an integer of 2 to 50.

8. A polyurethane composition as claimed in claim 7 wherein m is from 5 to 18.

9. A polyurethane composition as claimed in claim 7 wherein the molecular weight of the polyether macrodiol is from about 200 to about 5000.

10. A polyurethane composition as claimed in claim 7 wherein the molecular weight of the polyether macrodiol is from about 200 to about 1200.

11. A polyurethane composition as claimed in claim 1 wherein the diisocyanate is at least one of the following:
   4,4'-methylenediphenyl diisocyanate (MDI);
   methylene bis(cyclohexyl) diisocyanate (H12MDI);
   p-phenylene diisocyanate (p-PDI);
   trans-cyclohexane-1, 4-diisocyanate (CHDI) or a mixture of cis CHDI and trans CHDI;
   1,6-hexamethylene diisocyanate (DICH);
   2,4-toluene diisocyanate (2,4-TDI) or its isomers;
   p-tetramethylxylene diisocyanate (p-TMXDI); and
   m-tetramethylxylene diisocyanate (m-TMXDI).

12. A material having improved mechanical properties, clarity, processability and/or degradation resistance comprising a polyurethane elastomeric composition as claimed in claim 1.

13. A degradation resistant material comprising a polyurethane elastomeric composition as claimed in claim 1.

14. A degradation resistant material as claimed in claim 13 wherein the material is in vivo degradation resistant.

15. A polyurethane composition of claim 1 wherein $R_1$, $R_2$, $R_3$ and $R_4$ are independently alkyl, alkenyl, alkynyl, aryl or heterocycle radicals.

16. A polyurethane composition of claim 15 wherein the alkyl radical is a straight chain, branched, mono-cyclic, or poly-cyclic alkyl radical.

17. A polyurethane composition of 16 wherein alkyl radical is selected from methyl; ethyl; propyl; isopropyl; butyl; isobutyl; sec-butyl; amyl; isoamyl; sec-amyl; 1,2-dimethylpropyl; 1,1-dimethylpropyl; pentyl; hexyl; 4-methylpentyl; 1-methylpentyl; 2-methylpentyl; 3-methylpentyl; 1,1-dimethylbutyl; 2,2-dimethylbutyl; 3,3-dimethylbutyl; 1,2-dimethylbutyl; 1,3-dimethylbutyl; 1,2,2-trimethylpropyl; 1,1,2-trimethylpropyl; heptyl; 5-methylhexyl; 1-methylhexyl; 2,2-dimethylpentyl; 3,3-dimethylpentyl; 4',4-dimethylpentyl; 1,2-dimethylpentyl; 1,3-dimethylpentyl; 1,4-dimethylpentyl; 1,2,3-trimethylbutyl; 1,1,2-trimethylbutyl; 1,1,3-trimethylbutyl; octyl; 6-methylheptyl; 1-methylheptyl; 1,1,3,3-tetramethylbutyl; nonyl; 1-, 2-, 3-, 4-, 5-, 6- or 7-methyloctyl; 1-, 2-, 3-, 4-or 5-ethylheptyl; 1-, 2- or 3-propylhexyl; decyl; 1-, 2-, 3-, 4-, 5-, 6-, 7- and 8-methylnonyl; 1-, 2-, 3-, 4-, 5- or 6-ethyloctyl; 1-, 2-, 3- or 4-propylheptyl; undecyl 1-, 2-, 3-, 4-, 5-, 6-, 7-, 8- or 9-methyldecyl; 1-, 2-, 3-, 4-, 5-, 6- or 7-ethylnonyl; 1-, 2-, 3-, 4- or 5- propyloctyl; 1-, 2-, or 3-butylheptyl; 1-pentylhexyl; dodecyl; 1-, 2-, 3-, 4-, 5-, 6-, 7-, 8-, 9- or 10-methylundecyl; 1-, 2-, 3-, 4-, 5-, 6-, 7- or 8-ethyldecyl; 1-, 2-, 3-, 4-, 5- or 6-propylnonyl; 1-, 2-, 3- or 4-butyloctyl; 1,2-pentylheptyl; cyclopropyl; cyclobutyl; cyclopentyl; cyclohexyl; cycloheptyl; cyclooctyl; cyclononyl and cyclodecyl.

18. A polyurethane composition of claim 15 wherein the alkenyl radical is a straight chain, branched, mono-cyclic or poly-cyclic alkene.

19. A polyurethane composition of claim 18 wherein the alkenyl radical is vinyl; allyl; 1-methylvinyl; butenyl; isobutenyl; 3-methyl-2-butenyl; 1-pentenyl; cyclopentenyl; 1-methyl-cyclopentenyl; 1-hexenyl; 3-hexenyl; cyclohexenyl; 1-heptenyl; 3 heptenyl; 1-octenyl; cyclooctenyl; 1-nonenyl; 2-nonenyl; 3-nonenyl; 1-decenyl; 3-decenyl; 1,3-butadienyl; 1,4-pentadienyl; 1,3-cyclopentadienyl; 1,3-hexadienyl; 1,4-hexadienyl; 1,3-cyclohexadienyl; 1,4-cyclohexadienyl; 1,3-cycloheptadienyl; 1,3,5-cycloheptatrienyl or 1,3,5,7-cycloocta-tetraenyl.

20. A polyurethane composition of claim 15 wherein the alkynyl radical is a straight chain, branched or mono-cyclic or poly-cyclic alkynyl.

21. A polyurethane composition of claim 20 wherein the alkynyl radical is ethynyl; 1-propynyl; 1- and 2-butynyl; 2-methyl-2-propynyl; 2-pentynyl; 3-pentynyl; 4-pentynyl; 2-hexynyl; 3-hexynyl; 4-hexynyl; 5-hexynyl; 10-undecynyl; 4-ethyl-1-octyn-3-yl; 7-dodecynyl 9-dodecynyl; 10-dodecynyl; 3-methyl-1-dodecynyl-3-yl; 2-tridecynyl; 11-tridecynyl; 3-tetradecynyl; 7-hexadecynyl or 3-octadecynyl.

22. A polyurethane composition of claim 15 wherein the aryl radical is single, polynuclear, conjugated or a fused residue of aromatic hydrocarbon.

23. A polyurethane composition of claim 22 wherein the aryl radical is phenyl; biphenyl; terphenyl; quaterphenyl; phenoxyphenyl; naphthyl; tetrahydronaphthyl; anthracenyl; dihydroanthracenyl; benzanthracenyl; dibenzanthracenyl or phenanthrenyl.

24. A polyurethane composition of claim 15 wherein the heterocycle radical is a mono-cyclic or poly-cyclic heterocycle group containing at least one heteroatom selected from nitrogen, sulphur and oxygen.

25. A polyurethane composition of claim 24 wherein the heterocycle radical is a N-containing heterocyclic group;
    unsaturated condensed heterocyclic group containing 1 to 5 nitrogen atoms;
    unsaturated 3 to 6-membered heteromonocyclic group containing 1 to 2 sulphur atoms;
    3 to 6-membered heteromonocyclic group containing 1 to 2 oxygen atoms and 1 to 3 nitrogen atoms;
    saturated 3 to 6-membered heteromonocyclic group containing 1 to 2 oxygen atoms and 1 to 3 nitrogen atoms;
    unsaturated condensed heterocyclic group containing 1 to 2 oxygen atoms and 1 to 3 nitrogen atoms;
    unsaturated 3 to 6-membered heteromonocyclic group containing 1 to 2 sulphur atoms and 1 to 3 nitrogen atoms;
    saturated 3 to 6-membered heteromonocyclic group containing 1 to 2 sulphur atoms and 1 to 3 nitrogen atoms; or,
    unsaturated condensed heterocyclic group containing 1 to 2 sulphur atoms and 1 to 3 nitrogen atoms.

26. A polyurethane composition of claim 15 wherein $R_7$ is an alkylene, alkenylene, alkynylene, arylene or heterocyclylene radical.

27. A polyurethane composition of claim 26 wherein the alkenylene radical is the alkenylene equivalent of the alkyl radicals claimed in claim 16 or claim 17.

28. A polyurethane composition as claimed of claim 26 wherein the alkenylene radical is the alkenylene equivalent of the alkenyl radical claimed in claim 18 or claim 19.

29. A polyurethane composition of claim 26 wherein the alkynylene radical is the alkynylene equivalent of the alkynyl radicals claimed in claim 20 or claim 21.

30. A polyurethane composition of claim 26 wherein the arylene radical is a single; polynuclear; conjugated or fused residue of an aromatic hydrocarbon.

31. A polyurethane composition of claim 30 wherein the arylene radical is phenylene, biphenylene, terphenylene, quaterphenylene, phenoxyphenylene, naphthylene, tetrahydronaphthylene, anthracenylene, dihyroanthracenylene, benzanthracenylene, dibenzanthracenylene or phenanthrenylene.

32. A polyurethane composition of claim 26 wherein the heterocycle radical is a mono-cyclic or poly-cyclic heterocyclyl group containing at least one heteroatom selected from nitrogen, sulphur and oxygen.

33. A polyurethane composition of claim 32 wherein the heterocyclene radical is N-containing heterocyclic group;
    saturated 3 to 6-membered heteromonocyclic group containing 1 to 4 nitrogen atoms;
    unsaturated condensed heterocyclic group containing 1 to 5 nitrogen atoms;
    unsaturated 3 to 6-membered heteromonocyclic group containing an oxygen atom;
    unsaturated 3 to 6-membered heteromonocyclic group containing 1 to 2 sulphur atoms;
    unsaturated 3 to 6-membered heteromonocyclic group containing 1 to 2 oxygen atoms and 1 to 3 nitrogen atoms;
    saturated 3 to 6-membered heteromonocyclic group containing 1 to 2 oxygen atoms and 1 to 3 nitrogen atoms;
    unsaturated condensed heterocyclic group containing 1 to 2 oxygen atoms and 1 to 3 nitrogen atoms;
    unsaturated 3 to 6-membered heteromonocyclic group containing 1 to 2 sulphur atoms and 1 to 3 nitrogen atoms;
    saturated 3 to 6-membered heteromonocyclic group containing 1 to 2 sulphur atoms and 1 to 3 nitrogen atoms; or,
    unsaturated condensed heterocyclic group containing 1 to 2 sulphur atoms and 1 to 3 nitrogen atoms.

34. A polyurethane composition of claim 15 wherein $R_7$ is a divalent linking group selected from O, S, and NR, wherein R is hydrogen; an optionally substituted straight chain; or a branched or cyclic, saturated or unsaturated hydrocarbon radical.

35. A polyurethane composition of claim 15 wherein the optionally substituted radical of $R_1$, $R_2$, $R_3$, $R_4$, R5, R and/or $R_7$ is substituted with one or more groups selected from oxygen; nitrogen; sulphur; alkyl; alkenyl; alkynyl; aryl; halo; haloalkyl; haloalkenyl; haloalkynyl; haloaryl; hydroxy; alkoxy; alkenyloxy; alkynyloxy; aryloxy; carboxy; benzyloxy; haloalkoxy; haloakenyloxy; haloakynyloxy; haloaryloxy; nitro; nitroalkyl; nitroalkenyl; nitroalkynyl; nitroaryl; nitroheterocyclyl; azido; amino; alkylamino; alkenylamino; alkynylamino; arylamino; benzylamino; acyl; akenylacyl; alkynylacyl; arylacyl; acylamino; acyloxy; aldehydo; alkylsulphonyl; arylsulphonyl; alkylsulphonylamino; arylsulphonylamino; alkylsulphonyloxy; arylsulphonyloxy; heterocyclyl; heterocycloxy; heterocyclylamino; haloheterocyclyl; alkylsulphenyl; arylsulphenyl; carboalkoxy; carboaryloxy; mercapto; alkylthio; arylthio; and acylthio.

36. A polyurethane composition of claim 15 wherein the silicon-containing diol is 1,3-bis(4-hydroxybutyl) tetramethyl disiloxane; 1,4-bis(3-hydroxypropyl) tetramethyl disilylethylene; or 1-4-bis(3-hydroxypropyl) tetramethyl disiloxane.

37. A polyurethane composition of claim 15 further comprising at least two chain extenders.

38. A polyurethane composition of claim 37 wherein at least one of the chain extenders is selected from 1,4-butanediol; 1,6-hexanediol; 1,8-octanediol; 1,9-nonanediol; 1,10-decanediol; 1,12-dodecanediol; 1,4-cyclohexanedimethanol; p-xylene glycol and 1,4-bis(2-hydroxyethoxy)benzene.

39. A polyurethane composition of claim 38 wherein the silicon-containing diol is present in the chain extender in the range of from 1 to 50 molar percent.

40. A polyurethane composition of claim 1 wherein n is 0, 1, or 2.

41. A polyurethane composition of claim 1, wherein the soft segment macrodiol is selected from the group consisting of polyester, polysiloxane, polycarbonate and polyether of formula (II):

  (II)

or mixtures thereof; wherein m is an integer of 4 or more, and p is an integer of 2 to 50.

42. A polyurethane composition of claim 1, wherein the soft segment macrodiol comprises polysiloxane macrodiol and polyether macrodiol of formula (II):

  (II)

wherein
m is an integer of 4 or more, and p is an integer of 2 to 50 or mixtures thereof.

43. A biomaterial comprising a polyurethane elastomeric composition as claimed in claim 1.

44. A polyurethane elastomeric composition comprising a reaction product of:
(i) macrodiols including:
(a) polysiloxane macrodiol; and
(b) polyether macrodiol;
(ii) MDI; and
(iii) chain extender composition including 1,4-butanediol and a silicon chain extender selected from 1,3-bis(4-hydroxybutyl)tetramethyl disiloxane, 1,4-bis(3-hydroxypropyl)tetramethyl disilylethylene and 1,4-bis(3-hydroxypropyl)tetramethyl disiloxane.

45. A polyurethane composition as claimed in claim 44 wherein the silicon chain extender is present in an amount of about 40 mol % of the chain extender composition.

46. A polyurethane composition as claimed in claim 1 wherein the diisocyanate and the chain extender in the composition together have a weight percentage from 20 to 60 wt %.

47. A polyurethane composition as claimed in claim 44 wherein the weight ratio of polysiloxane to polyether is from 1:99 to 99:1.

48. A polyurethane composition as claimed in claim 47 wherein the weight ratio of polysiloxane to polyether is about 80:20.

* * * * *